(12) United States Patent
de Vocht et al.

(10) Patent No.: US 6,903,191 B2
(45) Date of Patent: Jun. 7, 2005

(54) METHOD OF PURIFYING A HYDROPHOBIN PRESENT IN A HYDROPHOBIN-CONTAINING SOLUTION

(75) Inventors: Marcel Leo de Vocht, Woerden (NL); Herman Abel B. Wösten, Zeist (NL); Joseph Gerard H. Wessels, Midlaren (NL)

(73) Assignee: Applied NanoSystems B.V., Groningen (NL)

(*) Notice: Subject to any disclaimer, the term of this patent is extended or adjusted under 35 U.S.C. 154(b) by 269 days.

(21) Appl. No.: 10/182,806

(22) PCT Filed: Feb. 2, 2001

(86) PCT No.: PCT/NL01/00083
§ 371 (c)(1),
(2), (4) Date: Nov. 25, 2002

(87) PCT Pub. No.: WO01/57076
PCT Pub. Date: Aug. 9, 2001

(65) Prior Publication Data
US 2003/0166960 A1 Sep. 4, 2003

(30) Foreign Application Priority Data
Feb. 4, 2000 (GB) .............................................. 0002661

(51) Int. Cl.$^7$ .................................................. C07K 1/00
(52) U.S. Cl. ...................................... 530/350; 530/350
(58) Field of Search ............................ 530/350; 560/1; 210/660; 427/372.2, 331

(56) References Cited

U.S. PATENT DOCUMENTS

2003/0134042 A1 * 7/2003 de Vocht et al. ......... 427/372.2

* cited by examiner

Primary Examiner—Karen Cochrane Carlson
Assistant Examiner—Agnes Rooke
(74) Attorney, Agent, or Firm—Norris McLaughlin & Marcus PA

(57) ABSTRACT

The invention relates to a method of purifying a hydrophobin present in a hydrophobin-containing solution. According to the invention the solution is contacted with a surface for the adsorption to that surface, and separated from a solution depleted in hydrophobin. Subsequently the surface is contacted with a solution containing a surfactant at a temperature lower than 90° C. Desorbed hydrophobin is separated from said surface.

11 Claims, No Drawings

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Conserved sequence of hydrophobins
<220> FEATURE:
<221> NAME/KEY: MISC_FEATURE
<222> LOCATION: (1)..(1)
<223> OTHER INFORMATION: Xaa represents any amino acid.
<220> FEATURE:
<221> NAME/KEY: MISC_FEATURE
<222> LOCATION: (3)..(3)
<223> OTHER INFORMATION: Xaa represents any amino acid.
<220> FEATURE:
<221> NAME/KEY: MISC_FEATURE
<222> LOCATION: (6)..(6)
<223> OTHER INFORMATION: Xaa represents any amino acid.
<220> FEATURE:
<221> NAME/KEY: MISC_FEATURE
<222> LOCATION: (8)..(8)
<223> OTHER INFORMATION: Xaa represents any amino acid.
<220> FEATURE:
<221> NAME/KEY: MISC_FEATURE
```

```
<222> LOCATION: (10)..(10)
<223> OTHER INFORMATION: Xaa represents any amino acid.
<220> FEATURE:
<221> NAME/KEY: MISC_FEATURE
<222> LOCATION: (13)..(13)
<223> OTHER INFORMATION: Xaa represents any amino acid.
<220> FEATURE:
<221> NAME/KEY: MISC_FEATURE
<222> LOCATION: (15)..(15)
<223> OTHER INFORMATION: Xaa represents any amino acid.

<400> SEQUENCE: 1

Xaa Cys Xaa Cys Cys Xaa Cys Xaa Cys Xaa Cys Cys Xaa Cys Xaa
1               5                   10                  15

<210> SEQ ID NO 2
<211> LENGTH: 17
<212> TYPE: PRT
<213> ORGANISM: Artificial Sequence
<220> FEATURE:
<223> OTHER INFORMATION: Sequence of hydrophobins as defined in the
      present invention
<220> FEATURE:
<221> NAME/KEY: MISC_FEATURE
<222> LOCATION: (1)..(1)
<223> OTHER INFORMATION: Xaa represents any amino acid.
<220> FEATURE:
<221> NAME/KEY: MISC_FEATURE
<222> LOCATION: (3)..(3)
<223> OTHER INFORMATION: Xaa represents any amino acid.
<220> FEATURE:
<221> NAME/KEY: MISC_FEATURE
<222> LOCATION: (5)..(5)
<223> OTHER INFORMATION: Xaa represents any amino acid.
<220> FEATURE:
<221> NAME/KEY: MISC_FEATURE
<222> LOCATION: (7)..(7)
<223> OTHER INFORMATION: Xaa represents any amino acid.
<220> FEATURE:
<221> NAME/KEY: MISC_FEATURE
<222> LOCATION: (9)..(9)
<223> OTHER INFORMATION: Xaa represents any amino acid
<220> FEATURE:
<221> NAME/KEY: MISC_FEATURE
<222> LOCATION: (11)..(11)
<223> OTHER INFORMATION: Xaa represents any amino acid.
<220> FEATURE:
<221> NAME/KEY: MISC_FEATURE
<222> LOCATION: (13)..(13)
<223> OTHER INFORMATION: Xaa represents any amino acid.
<220> FEATURE:
<221> NAME/KEY: MISC_FEATURE
<222> LOCATION: (15)..(15)
<223> OTHER INFORMATION: Xaa represents any amino acid.
<220> FEATURE:
<221> NAME/KEY: MISC_FEATURE
<222> LOCATION: (17)..(17)
<223> OTHER INFORMATION: Xaa represents any amino acid.

<400> SEQUENCE: 2

Xaa Cys Xaa Cys Xaa Cys Xaa Cys Xaa Cys Xaa Cys Xaa Cys Xaa
1               5                   10                  15

Cys Xaa
```

METHOD OF PURIFYING A HYDROPHOBIN PRESENT IN A HYDROPHOBIN-CONTAINING SOLUTION

This application is a national stage application of PCT/NL01/00083, filed on Feb. 2, 2001, which claims foreign priority from UK 0002661.7, filed on Feb. 4, 2000.

The present invention relates to a method of purifying a hydrophobin present in a hydrophobin-containing solution.

Hydrophobins are proteins known for their capability of forming a water-insoluble coating on a surface of an object. The adherence is so strong that the coating can not be removed by boiling in a 2% sodium dodecylsulfate (SDS) solution. Indeed, it has been suggested to coat a surface of, for example a biosensor, with a hydrophobin to modify the hydrophobic/hydrophillic nature of said surface. A hydrophobin-containing solution should be handled with care, as actions such as shaking result in turbid solutions containing hydrophobin aggregates which affect a uniform coating of a surface. For the application of a hydrophobin on a significant scale, an industrial scale method is necessary for purifying a hydrophobin present in a hydrophobin-containing solution, such as growth medium of a fermentation. The method according to the state of the art relies on the use of trifluoroacetic acid (TFA), which is for environmental and safety reasons not desirable.

To this end the present invention provides a method according to the preamble, characterized in that the hydrophobin-containing solution is contacted with a surface for adsorption to that surface, separation of the surface carrying adsorbed hydrophobin and a solution depleted in hydrophobin, after which the surface carrying adsorbed hydrophobin is contacted with a solution containing a surfactant at a temperature lower than 90° C. to solubilize the hydrophobin adsorbed to said surface and separating a hydrophobin-enriched surfactant-comprising solution from said surface.

Surprisingly it has been found that, provided that the temperature condition is met, hydrophobin can be eluted from a surface to which it is adsorbed. It goes without saying that the surface is the surface of an object having a high surface to volume ratio. To prevent any irreversible changes in structure, rendering the hydrophobin insoluble, the surface carrying hydrophobin should not be subjected to temperatures exceeding 90° C. before being contacted with the solution containing surfactant.

Hydrophobins are a well-defined class of proteins (ref. 1) capable of self-assembly at a hydrophobic-hydrophilic interface, and having a conserved sequence

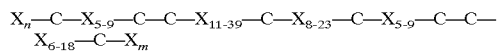

X, of course, represents any amino acid, and n and m, of course, independently represent an integer. In general, a hydrophobin has a length of up to 125 amino acids. The cysteine residues (C) in the conserved sequence are part of disulfide bridges. In the present invention, the term hydrophobin has a wider meaning to include functionally equivalent proteins, and encompasses a group of proteins comprising the sequence or parts thereof

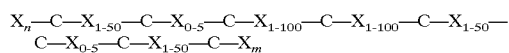

still displaying the characteristic of self-assembly at a hydrophobic-hydrophilic interface resulting in a protein film. In accordance with the definition of the present invention, self-assembly can be detected by adsorbing the protein to Teflon and use Circular Dichroism to establish the presence of a secondary structure (in general α-helix) (ref. 2). The formation of a film can easily be established by incubating a Teflon sheet in the protein solution followed by at least three washes with water or buffer (ref. 3). The protein film can be visualised by any method, such as labeling with a fluorescent compound or by the use of fluorescent antibodies, as is well established in the art. m and n may have values ranging from 0 to 2000. Included in the definition are fusion-proteins of a hydrophobin and another protein as such recombinant proteins may similarly be purified with the method according the present invention.

WO-A-9641882 describes in a general fashion purification of hydrophobins using precipitation and chromatographic methods, in particular precipitation using methanol, ethanol, acetone and ammonium sulphate, and ion exchange and hydroxy apatite chromatography. SDS is mentioned as helpful when isolating hydrophobin from the cells in which it is produced and from culture medium in which they are present.

Martin G. G. et al. describe in J. Am. Chem. Soc. vol. 39 (1), p. 347–348 (1998) a method of purifying hydrophobin using preparative electrophoresis, followed by hydroxy apatite chromatography to remove SDS.

Preferably the temperature is lower than 60° C., such as lower than 40° C., in particular lower than 20° C., and more preferably lower than 10° C.

In general, is the concentration of the surfactant between 0.001% and 5% (w/v), advantageously between 0.01% and 1.0% (w/v), preferably between 0.02% and 0.1%.

Suitable concentrations surfactant can easily be determined using various spectroscopic techniques such as circular dichroism (CD) such as described by De Vocht et al (ref. 2) or Infra Red (IR) spectroscopy (ibid). Alternatively, it is possible to determine a suitable concentration surfactant by simple trial and error: A surface is coated with a hydrophobin-containing solution, and said surface is treated with the solution containing the surfactant after which the presence of hydrophobin is investigated using, for example, fluorescence-based or radioactivity-based techniques. Although it is possible to use suitably labelled antibodies against hydrophobin, it is easier to coat the surface with labelled hydrophobin and detect the amount of label remained in comparison with a surface treated with the same solution but without surfactant.

According to a further embodiment, the hydrophobin is solubilized under a pressure of at least 1.1 Bar.

Elevated pressures facilitate the elution of the adsorbed hydrophobin from the surface carrying adsorbed hydrophobin.

According to another preferred embodiment, the pressure is reduced during adsorption of the hydrophobin at the surface.

Reducing the pressure during adsorption facilitates the adsorption of the hydrophobin to the surface. In general, the pressure of the hydrophobin-containing solution will have a pressure of at least 1.1 Bar when the solution is first contacted with the surface.

In principle, the surface at which the hydrophobin is to be adsorbed, may be of any material, such as glass or plastic. Preferably the surface has a contact angle for water larger than 60°. Such a contact angle makes the surface very suitable for adsorbing hydrophobin present in the hydrophobin-containing solution.

According to a preferred embodiment, the surface is the surface of an object having a high surface-to-volume ratio. This allows for the purification of hydrophobin in a relatively small volume.

The invention will now be illustrated by way of the following examples.

Methods

A) Secondary Structure Measurements

The secondary structure of a hydrophobin was studied with circular dichroism spectroscopy (CD). The CD-spectra were recorded over the wavelength region 190–250 nm on an Aviv 62A DS CD spectrometer (Aviv Associates, Lakewood, N.J., USA), using a 1-mm quartz cuvette and following a known procedure (2). The sample compartment was continuously flushed with $N_2$ gas and the temperature was kept constant at 25° C. 10 scans were averaged, using a bandwidth of 1 nm, a stepwidth of 1 nm, and 1 sec averaging per point. The spectra were corrected using a reference solution without the protein. Typically a protein concentration of 10 $\mu$M in 50 mM phosphate pH 7.0 was used. For spectra of SC3 bound to a hydrophobic support, 130 nm unstabilized colloidal Teflon spheres (Dupont de Nemours, Geneva, Switzerland) in water were added to the solution.

B) Binding to Teflon

The coating of Teflon (Norton Fluorplast B. V., Raamsdonksveer, The Netherlands) by SC3 was assessed essentially as described by Wösten et al. (3). Thoroughly cleaned (ref. 3) Teflon sheets were incubated for 16 hours in 20 $\mu$g/ml $^{35}$S-labelled hydrophobin in water, followed by three washes with water for 10 minutes each. The amount of adsorbed $^{35}$S-labelled protein were determined by scintillation counting.

EXAMPLE 1

50 $\mu$g/ml SC3 in 50 mM phosphate buffer (pH=7.0) was mixed with 130 nm unstabilized colloidal Teflon spheres (Dupont de Nemours, Geneva, Switzerland) at 25° C. SC3 adsorbed to the surface of the Teflon and attained the α-helical state (calculated surface coverage 9%).

The spheres were treated with 0.1% w/v Tween-20 or 0.1% v/w Tween-80 at 25° C. for 10 minutes and spun down (1 min; 10,000 g). Substantially 100% of SC3 desorbed after addition of the detergent and attained the monomeric state. As expected, in the absence of detergent SC3 remained adsorbed (in the α-helical state as determined by CD).

EXAMPLE 2

Teflon sheets (2 $cm^2$, thickness 0.25 mm) were incubated in 20 $\mu$g/ml $^{35}$S-labelled SC3 overnight at room temperature. The SC3-coated sheets were subsequently washed with water at room temperature. The sheets were then treated with 2% Tween 20 (pH 7.0) or water (control), either at room temperature or 100° C. (control) for 30 min. After this treatment, the sheets were removed. The amount of radioactive SC3 released into the supernatant obtained after centrifugation (1 min; 10,000 g) was determined. Percentages are relative to the amount of radioactivity originally bound to the sheet.

TABLE 1

The amount of radioactive SC3 released into the supernatant obtained after centrifugation.

| | % SC3 released | |
|---|---|---|
| | room temperature | 100° C. |
| 2% Tween 20 | 78% | 6% |
| Water (control) | 6% | 7% |

This shows that a surfactant may be used to elute a hydrophobin provided the temperature requirement is met.

References

1. Wessels, J. G. H. (1997) in Adv. Microb. Physiol. 38, 1–45.
2. De Vocht, M. L., et al. (1998) in Biophys. J. 74, 2059–68.
3. Wösten, H. A. B., et al. (1994) in Embo. J. 13, 5848–54.

What is claimed is:

1. A method for purifying hydrophobin, said method comprising:
   a) contacting the hydrophobin-containing solution with surface for adsorption to that surface,
   b) separating the surface carrying adsorbed hydrophobin and solution depleted in hydrophobin,
   c) contacting the surface carrying adsorbed hydrophobin with a solution containing a surfactant at a temperature lower than 90° Centigrade to solubilize the hydrophobin adsorbed to said surface, and
   d) separating a hydrophobin-enriched surfactant-comprising solution from said surface.

2. Method according to claim 1, wherein the temperature is lower than 60° C.

3. Method according to claim 1, wherein the temperature is lower than 40° C.

4. Method according to claim 1, wherein the temperature is lower than 20° C.

5. Method according to claim 1, wherein the temperature is lower than 10° C.

6. Method according to claim 1, wherein the concentration of the surfactant is between 0.001% and 5% (w/v).

7. Method according to claim 1, wherein the concentration of the surfactant is between 0.01% and 1.0% (w/v).

8. Method according to claim 1, wherein the concentration of the surfactant is between 0.02% and 0.1% (w/v).

9. Method according to claim 1, wherein the hydrophobin is solubilized under a pressure of at least 1.1 Bar.

10. Method according to claim 1, wherein during adsorption of the hydrophobin at the surface, the pressure is reduced.

11. Method according to claim 1, wherein the surface has a contact angle for water larger that 60°.

* * * * *